United States Patent [19]
Wong et al.

[11] Patent Number: 6,001,357
[45] Date of Patent: Dec. 14, 1999

[54] METHOD OF ENHANCING WOUND HEALING WITH ANTI-IL-5 ANTIBODY

[75] Inventors: David T. W. Wong, Newton; Peter F. Weller, Wellesley, both of Mass.

[73] Assignee: Shering-Plough, Kenilworth, N.J.

[21] Appl. No.: 09/143,467

[22] Filed: Aug. 27, 1998

Related U.S. Application Data

[60] Provisional application No. 60/057,108, Aug. 27, 1997.

[51] Int. Cl.$^6$ .......................... A61K 39/395; C07K 16/24
[52] U.S. Cl. ..................... 424/145.1; 424/130.1; 424/141.1; 424/158.1; 424/152.1; 424/172.1; 530/387.1; 530/388.1; 530/388.2; 530/388.23; 530/388.7
[58] Field of Search ............................. 424/130.1, 141.1, 424/158.1

[56] References Cited

U.S. PATENT DOCUMENTS 5,510,339  4/1996  Gleich et al. .

OTHER PUBLICATIONS

Hom et al., Clin. Immunol. Immunopathol., 73: 305–311, 1994.
Debets et al., Immunol. Today, 15: 45–458, 1994.
The Merck Manual, Sixteenth Edition, p. 646, Merck Research Laboratories Rahway, NJ, 1992.
Kaplan, et al. Novel Responses of Human Skin to Intradermal Recombinant Granulocyte/Macrophage–Colony–stimulating Factor: Langerhans Cell Recruitment, Keratinocyte Growth, and Enhanced Wound Healing. J. Exp. Med. Jun. 1992, vol. 175, pp. 1717–1728.
Todd, et al. The Eosinophil as a Cellular Source of Transforming Growth Factor Alpha in Healing Cutaneous Wounds. American Journal of Pathology. Jun. 1991, vol. 138, No. 6, pp. 1307–1313.
Yang, et al. Depletion of Eosinophil Infiltration by Anti–IL–5 Monoclonal Antibody (TRFK–5) Accelerates Open Skin Wound Epithelial Closure. Amerian Journal of Pathology. Sep. 1997, vol. 151, No. 3, pp. 813–819, especially pp. 816–817.
Bassett et al., 1977, *Br. J. Exp. Pathol.*, 58:581–605.
Berthet et al., 1994, *Brit. J. Surg.*, 81:395–398.
Bjorck et al., 1997, *Digestive Diseases and Sciences*, 42:824–832.
Brown et al., 1995, *Otolaryngolic Clinics of North America*, 28:1081–1091.
Coffman et al., 1989, *Science*, 245:308–310.
de Waard et al., 1995, *Arch. Surg.*, 130:959–965.
Elovic et al., 1990, *Am. J. Pathol.*, 137:1425–1434.
Frimm et al., 1996, *J. Mol.Cell Cardiol.*, 28:1279–1285.
Hibbs et al., 1982, *Biochem. J.*, 207:621–624.
Khandwala et al., 1997, *Oral Surg. Oral Med. Oral Path.*, 83:222–230.
Konturek t al., 1997, *Euro. J. Pharm.*, 322:73–77.
Korkina et al., 1995, *Nutrition*, 11:555–558.
Nebiki et al., 1997, *J. Gastroenterology and Hepatology*, 12:109–114.
Oxynoid et al., 1994, *Art. Cells, Blood Subs., and Immob. Biotech.*, 22:1331–1336.
Pierce et al., 1989, *J. Cell Biol.*, 109:429–440.
Quaglino et al., 1990, *Lab. Invest.*, 63:307–319.
Rikimaru et al., 1993, *Nippon Kyobu Shikkan Gakkai Zasshi*, 31:426–430.
Schreiber et al., 1986, *Science*, 232:1250–1253.
Spry and Tai, 1976, *Clin. Exp. Immunol.*, 24:423–434.
Takahashi et al., 1995, *Biochem. Biophys. Res. Commun.*, 216:298–305.
Tominaga et al., 1997, *Digestion*, 58:120–128.
Tominaga et al., 1997 *Digestive Diseases and Sciences*, 42:616–625.
Weller, 1991, *N. Engl. J. Med.*, 324:1110–1118.
Wong et al., 1990, *J. Exp. Med.*, 172:673–81.
Wong et al., *Blood*, 1991, 78:2702–2707.
Wong et al., 1993, *Am. J. Path.*, 143:130–142.
Yang et al, 1996, *Am. J. Physiol.*, 270:G191–G202.

*Primary Examiner*—Christina Y. Chan
*Assistant Examiner*—Amy DeCloux
*Attorney, Agent, or Firm*—Banner and Whitcoff Ltd.; Kathleen Madden Williams

[57] ABSTRACT

The invention provides a method of enhancing wound healing, comprising administering an inhibitor of eosinophil influx into a wound site sufficient to result in healing of the wound.

1 Claim, 5 Drawing Sheets

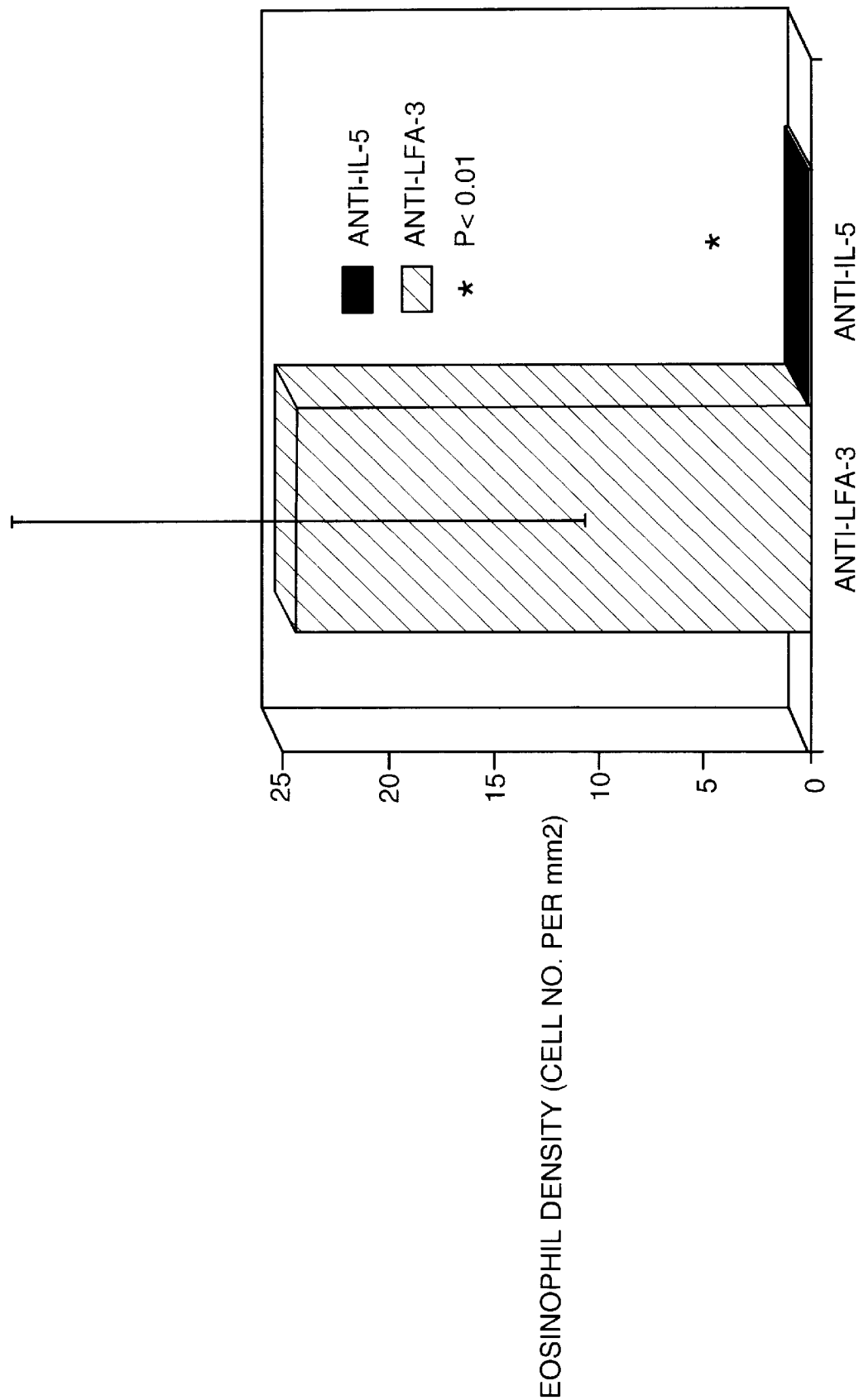

METHOD OF ENHANCING WOUND HEALING WITH ANTI-IL-5 ANTIBODY

The application claims the benefit of U.S. Provisional Application No. 60/057,108, filed Aug. 27, 1997.

This invention was supported by NIH Grant Nos. DE-10335, AI-20241, DE-00275, HL-46563, and DE-00312 and the government has certain rights to the invention.

FIELD OF THE INVENTION

The invention relates in general to the treatment of epithelial injury.

BACKGROUND OF THE INVENTION

Wound healing is a process critical to the survival of the species after injury. Twenty years ago, it was shown that eosinophils are components of the inflammatory infiltrate in rat incisional cutaneous wounds (Bassett et al., 1977, *Br. J. Exp. Pathol.,* 58: 581–605); however the importance of the presence of eosinophils remains unclear. Eosinophils have been implicated in the regulation of collagen metabolism (Hibbs et al., 1982, *Biochem. J.,* 207: 621–624) and have been shown to elaborate transforming growth factor-alpha (TGF-α) (Elovic et al., 1990, *Am. J. Pathol.,* 137: 1425–1434; Wong et al., 1990, *J. Exp. Med.,* 172: 673–81) and transforming growth factor-beta 1 (TGF-β1; Wong et al., *Blood,* 1991, 78: 2702–2707), two multifunctional cytokines of importance in wound healing (Schreiber et al., 1986, *Science,* 232: 1250–1253; Pierce et al., 1989, *J. Cell Biol.,* 109: 429–440; Quaglino et al., 1990, *Lab. Invest.,* 63: 307–319). In a hamster model, eosinophils have been demonstrated to infiltrate prominently into open skin wounds, where they represent a cellular source of TGF-α and TGF-β1 at both mRNA and protein levels (Wong et al., 1993, *Am. J. Path.,* 143: 130–142), and the expression of TGF-β1 and TGF-α by eosinophils in oral wounds has been characterized in some detail (Yang et al, 1996, *Am. J. Physiol.,* 270: G191-G202).

Eosinophils are a distinct lineage of granulocytes which originate from the bone marrow, circulate in the blood and emigrate into peripheral tissues (Spry, 1988, *Eosinophils,* ed. C. Spry, Oxford University Press, New York). Although eosinophils normally comprise only ~3% of circulating leukocytes in humans, large numbers of mature eosinophils are especially abundant near the mucosal surfaces of gastrointestinal, respiratory, and genitourinary tracts (Spry and Tai, 1976, *Clin. Exp. Immunol.,* 24: 423–434). In addition, greatly increased numbers of eosinophils appear in the blood and tissues associated with immune responses or disease processes such as helminthic parasitic infections, allergic diseases, and other pathological states with less well-defined causes (Weller, 1991, *N. Engl. J. Med.,* 324: 1110–1118).

SUMMARY OF THE INVENTION

The invention encompasses a method of enhancing wound healing, comprising administering to a mammal in need thereof an amount of an inhibitor of eosinophil influx into a wound site sufficient to result in healing of a wound.

As used herein, the term "wound" is defined as any break in the epithelium. Such breaks may result from a cut, abrasion, adhesion, surgical incision, thermal-, chemical- or friction burn or ulcer, and may be either external or internal.

The term "enhancing", when used herein in reference to wound healing, is defined as increasing the rate at which a healing occurs, wherein "healing" is defined as wound closure by re-epithelialization, such that the application of light pressure to the wound no longer results in leakage to the outside of a bodily fluid, e.g. blood or lymphatic fluid.

As used herein, the term "epithelium" refers to the internal and external surfaces of the body.

As used herein, the term "mammal" refers to any member of the Class Mammalia, including a human.

As used herein, the term "inhibitor" is defined as any substance which blocks the influx of eosinophils into a wound site, whether directly or by inhibiting a signalling pathway that results in such infiltration. The term "inhibitor" is further defined as that which blocks or reverses the effect of eosinophil infiltration once such infiltration has occurred. Such blocking or reversal may occur at the level of synthesis of a substance produced by an eosinophil. Alternatively, it may be the native activity of such a substance which is blocked or reversed, either directly, or by inhibition of downstream target molecules, e.g. in a signalling cascade or biosynthetic pathway. An inhibitor may exert an opposing function (for example, activation of a receptor that is opposed by the substance being inhibited, or of a receptor that regulates a signalling cascade that results in an opposing function to that controlled by a receptor activated by the substance). An inhibitor may modify the substance produced by the infiltrating eosinophil, for example altering its state of phosphorylation or glycosylation or cleaving the substance. An inhibitor, such as an antibody, may bind to the substance and either sterically hinder an active site or change the conformation of the substance; it may also, in the case in which the substance acts in dimerized or multimerized form, be an inactive monomer which binds the substance and ties it up in a non-functional unit, which may either remain in place or be degraded by cellular mechanisms.

Preferably, the inhibitor inhibits a cytokine that influences the maturation of eosinophils, wherein inhibition of the cytokine results in inhibition of eosinophil influx into the wound; more preferably, this inhibitor inhibits a Colony Stimulating Factor (CSF); most preferably, this inhibitor inhibits IL-5.

As used here, the term "maturation" refers to the process by which hematopoietic stem cells become eosinophils.

Preferably, the inhibitor is an anti-IL-5 antibody.

Further features and advantages of the invention will become more fully apparent in the following description of the embodiments and drawings thereof, and from the claims.

BRIEF DESCRIPTION OF THE DRAWINGS

FIG. 2 presents a comparison of eosinophil density in day 9 cutaneous wounds of hamsters treated with anti-IL-5 monoclonal antibody or a control monoclonal antibody.

FIG. 3 shows the detection of eosinophil infiltration in day 9 cutaneous wounds of hamsters treated with anti-IL-5 monoclonal antibody or a control monoclonal antibody.

DESCRIPTION OF THE INVENTION

Figure 1:
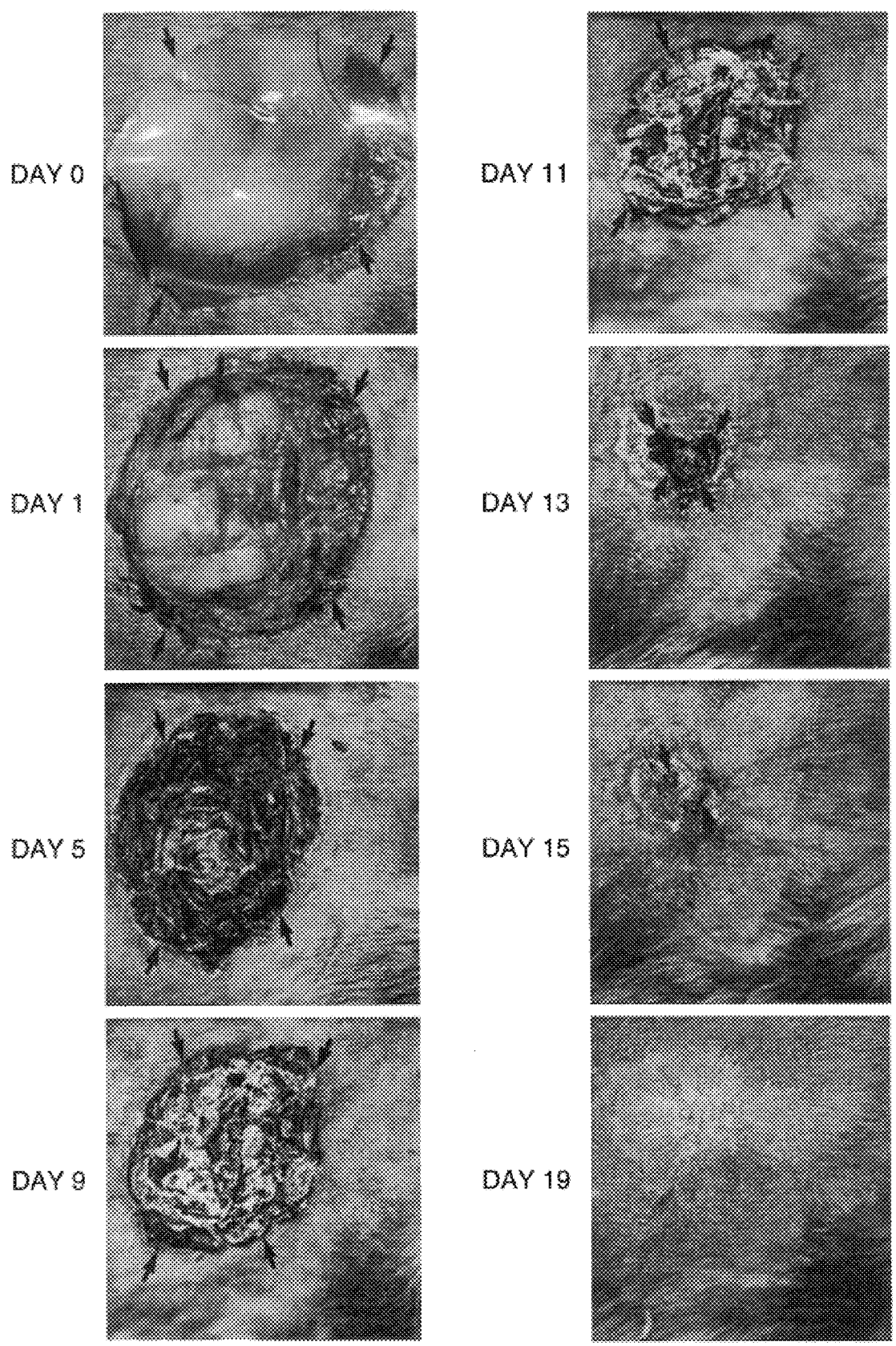
FIG. 1 depicts the progression of wound healing on hamster dorsal skin.
Figure 3A:
FIG. 3A depicts in bright-field view a 40× magnification of a mirror-image montage constructed from halves of a day-9 anti-IL-5-treated wound (right side) and a control wound (left side).
Figure 3B:
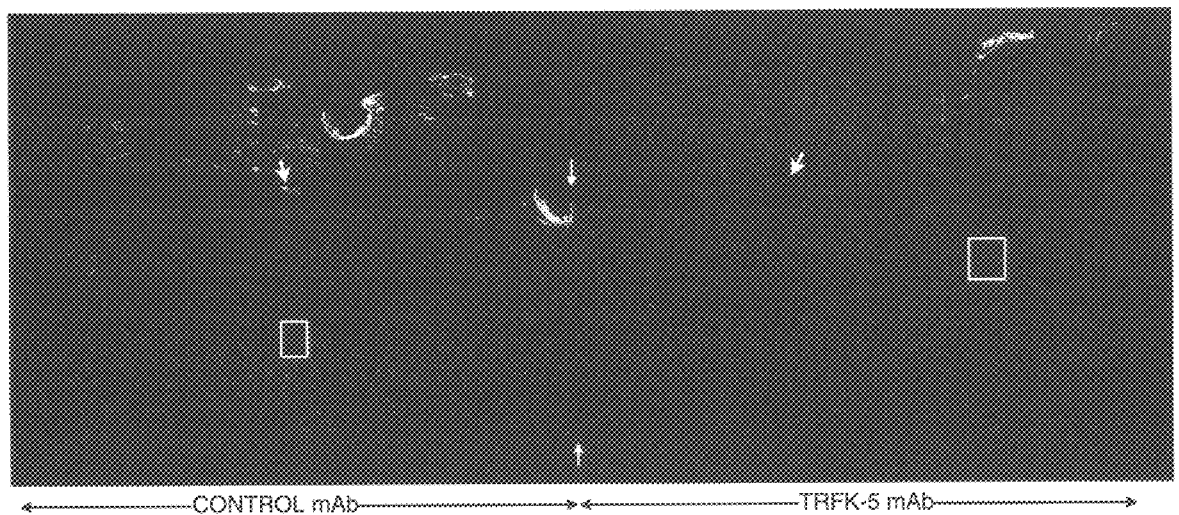
FIG. 3B presents a rhodamine fluorescence image at 100× magnification of the montage presented in FIG. 3A.
Figure 3C:
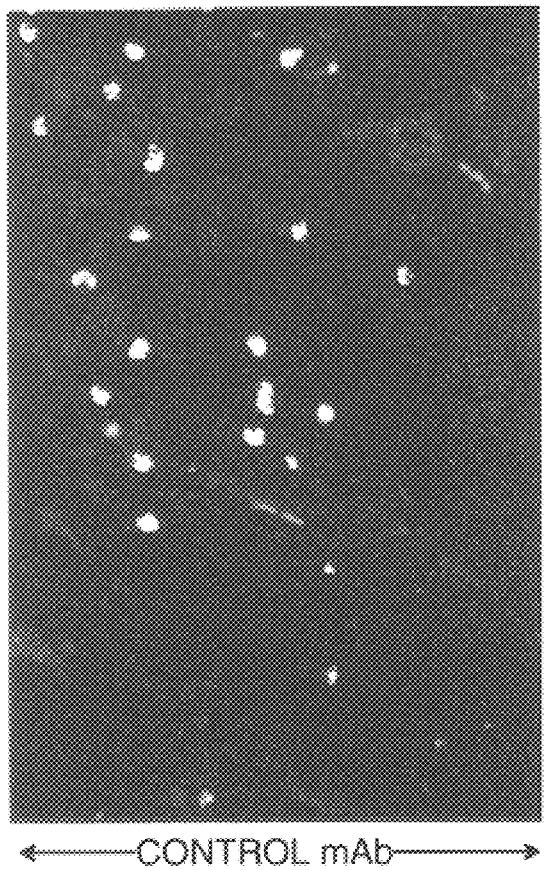
FIG. 3C presents a 600× magnification of the bracketed area of FIG. 3A, in which the identity of eosinophils was confirmed.
Figure 3D:
FIG. 3D presents a 600× magnification of the bracketed area of FIG. 3B, in which the identify of eosinophils was confirmed.

The invention is based on the recognition that inhibition of eosinophil influx into a wound results in enhanced wound healing. Animal models are described herein for wound healing via inhibition of eosinophil infiltration in the wound site.

Inhibitors Useful According to the Invention

Enhanced wound healing according to the methods of the invention, e.g. by blocking the effect of eosinophilia in wounded tissue, can be brought about by intervention at either of two levels.

First, the invention provides a means by which to counteract inhibition of the development of the broad group of cells categorized as leukocytes, of which eosinophils represent one member. Their development from various hematopoietic stem cells is mediated by the Colony Stimulating Factor (CSF) family of proteins. Administration of a CSF inhibitor is believed to be effective in blocking leukocyte development and function; the subset of leukocyte cell types affected is determined by the identity of the CSF molecule inhibited. Suitable direct inhibitors include CSF analogues (which would compete with a given CSF for binding to sites on receptors or other molecules), antisense RNA, CSF mRNA-specific ribozymes and antibodies directed at CSF proteins. By similar methods, CSF function can be inhibited indirectly, i.e. by blocking the synthesis or activities of downstream target molecules, such as signalling molecules or growth factors, that participate in the leukocyte induction pathway.

One CSF, interleukin-5 (IL-5), positively regulates the pathway that results in maturation, terminal differentiation and release of eosinophils (Yamaguchi et al., 1988, *J. Exp. Med.*, 167: 1737–1742); therefore, inhibition of the production or function of this molecule by any of the above methods may be performed according to the methods of the invention in order to negate the impact of eosinophil infiltration on wound healing. One specific inhibitor of IL-5 is TRFK-5 (supplied for these experiments by Schering-Plough Research Institute), a murine monoclonal antibody directed against human IL-5. This antibody is heterospecifically reactive; in other words, although the antibody was raised against a human protein, it recognizes IL-5 homologues in other species as well. Its use to inhibit eosinophilia in an animal model of wound healing is exemplified below in Example 2. Note that at least one other mouse monoclonal antibody directed against human IL-5 is commercially available (catalogue # MAB205, R & D Systems, Minneapolis, Minn.), and it is expected that this antibody can be used according to the methods of the present invention without undue experimentation or uncertainty on the part of one of average skill in the art. It is also possible to generate an anti-IL-5 antibody by methods well known in the art (see below). Purified, recombinant IL-5 protein against which to raise antibodies is commercially available; for example, human IL-5 can be obtained from R & D Systems, Minneapolis, Minn. (Cat. No. 205-IL), as can mouse IL-5 (Cat. No. 405-ML).

Second, counteracting the effects of eosinophils that have infiltrated a wound on tissue at that site will offset their negative effect on the rate of healing. To accomplish this, the invention provides for inhibition of the products of eosinophils, either directly or indirectly. Cell-type-specific proteins must first be identified, and their associations with wound-healing assessed. Inhibition of these proteins is expected to result in full or partial reversal of eosinophil-induced repression of wound healing. As stated above, the cytokines TGF-α and TGF-β1 are produced by eosinophils in wound tissue (Wong et al., 1993, supra), and are, as a result, good candidate target molecules for inhibition treatment of wounds. Although the mechanism by which eosinophils influence the rate of wound healing is not known, those in the post-acute phase of wound healing elaborate TGF-β1, which is anti-proliferative to keratinocytes (Wong et al., 1993, supra), suggesting a possible mechanism by which this eosinophil-specific protein inhibits wound healing.

An inhibitor of a cytokine or other product of eosinophils may comprise an analogue of that molecule, which may compete with the product for binding sites on a receptor or other molecule, an antisense RNA complementary to- or a ribozyme designed to cleave the message encoding the product or an antibody directed against the product. Any of the these several classes of inhibitors can, alternatively, be utilized to block a downstream target of the eosinophil product, e.g. in a signal transduction- or biosynthetic pathway, thereby indirectly inhibiting its action. Antibodies directed against the products of eosinophils are of particular use according to the methods of the invention. For example, antibodies directed against the cytokines TGF-α and TGF-β1 are publicly available; additional antibodies can be made by the methods well known in the art (see below).

A goat anti-human-TGF-α polyclonal antibody is commercially available (Cat. No. AB239NA; R & D Systems, Minneapolis, Minn.), as is a monoclonal antibody directed at amino acids 34–50 of the C-terminus of human TGF-α (Cat. No. TGF-α; Ab-2; GF-10; Oncogene Science, Uniondale, N.Y). The latter was used in the detection of TGF-α in wound tissue, as described in Example 4. Should these antibodies fail as inhibitors of TGF-α function, and it becomes necessary to raise additional antibodies, TGF-α protein can be derived from at least two cell lines available from ATCC: Catalogue No. CRL-2109 (FAT7), a rat squamous cell carcinoma line, and Catalogue No. CRL-2254 (AML), a transformed mouse liver hepatocyte line that produces both the mouse and human TGF-α proteins.

In the detection experiments described in Example 4, a rabbit anti-human TGF-β1 polyclonal antibody was used (Cat. No. AB-20-PB; R & D systems, Minneapolis, Minn.). Also available from R & D Systems are Cat. No. MAB240, a mouse anti-human-TGF-β1 monoclonal antibody and AB246NA, a goat anti-human-TGF-β1 polyclonal antibody. Should these antibodies prove ineffective at inhibiting the effects of eosinophilia, others can be prepared (see above). Two publically-available cell lines that produce TGF-β1 are as follows: ATCC Catalog Nos. CRL-2159 (LS411N) and CRL-2134 (LS513), the latter of which is a human cell line derived from caecal (colonic) tissue.

Generation of Antibodies

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

Preparation of Antibodies

1. Polyclonal antibodies.

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.*, 267: 4815–4823). The serum is titered against protein antigen by ELISA or alternatively by dot or spot blotting (Boersma and Van Leeuwen, 1994, *J. Neurosci. Methods*, 51: 317). At the same time, the antiserum may be used in tissue sections. The serum is shown to react strongly with the appropriate peptides by ELISA, for example, following the procedures of Green et al., 1982, *Cell*, 28: 477–487.

2. Monoclonal antibodies.

Techniques for preparing monoclonal antibodies are well known, and monoclonal antibodies may be prepared using any candidate antigen whose level is to be measured in wound tissue, such as a Colony Stimulating Factor (e.g. IL-5) or, as discussed below, a cytokine (e.g. TGF-α or TGF-β1), preferably bound to a carrier, as described by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" a protein.

Particularly preferred immunological tests rely on the use of either monoclonal or polyclonal antibodies and include enzyme-linked immunoassays (ELISA), immunoblotting and immunoprecipitation (see Voller, 1978, *Diagnostic Horizons*, 2: 1–7, Microbiological Associates Quarterly Publication, Walkersville, Md.; Voller et al., 1978, *J. Clin. Pathol.*, 31: 507–520; U.S. Reissue Pat. No. 31,006; UK Patent 2,019,408; Butler, 1981, *Methods Enzymol.*, 73: 482–523; Maggio, E. (ed.), 1980, *Enzyme Immunoassay*, CRC Press, Boca Raton, Fla.) or radioimmunoassays (RIA) (Weintraub, B., *Principles of radioimmunoassays*, Seventh Training Course on Radioligand Assay Techniques, The Endocrine Society, March 1986, pp. 1–5, 46–49 and 68–78). For analyzing wound tissues for the presence of a protein that is to be acted against by a candidate inhibitor according to the present invention, immunohistochemistry techniques are preferably used. It will be apparent to one skilled in the art that the antibody molecule will have to labeled to facilitate easy detection of a target protein. Techniques for labeling antibody molecules are well known to those skilled in the art (see Harlour and Lane, 1989, *Antibodies*, Cold Spring Harbor Laboratory, pp. 1–726).

Alternatively, other techniques can be used to detect the target proteins, including chromatographic methods such as SDS PAGE, isoelectric focusing, Western blotting, HPLC and capillary electrophoresis.

Monoclonal antibody-producing hybridomas (or polyclonal sera) can be screened for antibody binding to the target protein. By antibodies, we include constructions using the binding (variable) region of such antibodies, and other antibody modifications. Thus, an antibody useful in the invention may comprise whole antibodies, antibody fragments, polyfunctional antibody aggregates, or in general any substance comprising one or more specific binding sites from an antibody. The antibody fragments may be fragments such as Fv, Fab and F(ab')$_2$ fragments or any derivatives thereof, such as a single chain Fv fragments. The antibodies or antibody fragments may be non-recombinant, recombinant or humanized. The antibody may be of any immunoglobulin isotype, e.g., IgG, IgM, and so forth. In addition, aggregates, polymers, derivatives and conjugates of immunoglobulins or their fragments can be used where appropriate.

Methods for Testing Inhibition of Eosinophilia

In order to test the efficacy of inhibitors of eosinophil influx into a wound site, the candidate inhibitor is tested in an animal model of wound healing. Several animal models useful according to the invention are known in the art. A first requirement of such a model is demonstrated proof that eosinophils do, indeed, infiltrate wound tissue in that organism. Such a result has been obtained in several mammalian systems. Eosinophils have been found to be associated with cutaneous wounds in the rat (Bassett et al., 1977, supra; Hibbs et al., 1982, supra), rabbit (Erjefalt et al., 1996, *Am. J. Respir. Crit. Care Med.*, 153: 1666–74), hamster (Wong et al., 1993, supra; Yang et al., 1996, supra) and pig (unpublished data). Given that such observations also have been made in humans (see below), the results of inhibitor testing performed in any of these several systems will be applicable to the clinical treatment of human surface wounds. If uncertainty exists as to whether wounding at a given anatomical site is followed by eosinophil influx, this can be determined by the methods described in the art below.

Having first selected the experimental organism and wound site, the surface area, depth, shape and position of wound which can be easily monitored for change and which will heal over a convenient time course is decided, as is a method of wounding (e.g. by means of abrasion, incision, chemical burn, radiation, etc.). Circular wounds are preferred, as a simple measurement of diameter is all that is required to assess wound contraction. After establishing the parameters for wound healing in an untreated subject, a typical wound-healing experiment comprises test and control groups of animals that are comparably wounded on the same day. By "comparably", it is meant that wounds of the same shape, area and depth are made at the same anatomical location. One group receives an appropriate dosage of the candidate inhibitor in a compatible carrier, while the other is dosed only with the carrier, and healing, as defined below in Example 1, is monitored over the course of many days. At a point following the initial acute phase of injury, when inflammation is reduced and healing is in progress, half of the animals in either of the two groups is sacrificed. The wounds are harvested, sectioned and subjected to bioassays, some designed to measure the density of eosinophils that have infiltrated the tissue and others directed at the analysis of protein markers that are locally expressed. Results within each group are collated, and then compared to those derived from the other group. A positive result, i.e. one in which eosinophils are seen to be reduced in the wound tissue of test subjects relative to controls, or where there is a statistically-significant difference in the expression of eosinophil-associated biochemical markers, such as the cytokines TGF-α or TGF-β1, between the two groups, indicates that the candidate compound is therapeutically useful according to the invention. A 2- to 200-fold reduction in the density of eosinophils infiltrating wound tissue is required for a result to be considered positive. Preferably, the reduction is in the range of 200- to 1 000-fold, or even to 2000- to 10,000-fold. A linear relationship between eosinophil density and the levels of eosinophil-produced markers in wound tissue is assumed, such that the degree of reduction in the levels of eosinophil products correlates to the same extent of enhanced healing that would be observed following direct observation of a reduction of comparable magnitude in eosinophil density.

The levels of cytokines, e.g. TGF-α or TGF-β1, or other eosinophil-produced markers present in external epithelial wound tissue may be assayed by any of several means, as described by Wong et al. (1993, supra). These methods, which can be performed using the hamster cutaneous wound-healing model of Example 1, are described in Example 4, while methods applicable to the detection of eosinophil proteins and nucleic acids in internal epithelial wound tissue are discussed in Examples 5 through 8. These methods can be summarized briefly, as follows:

a) Northern analysis of eosinophil-associated mRNA in sectioned wound tissue.

b) In situ hybridization of labeled nucleic acid probes to detect eosinophil-associated transcripts in fixed sections of wound tissue.

c) PCR analysis of eosinophil-associated mRNA in wound tissue.

d) Immunocytochemical analysis in fixed, sectioned wound tissue of proteins produced by eosinophils.

e) Western analysis of eosinophil protein products extracted from wound tissue. In the wound of an untreated test subject, observed levels of eosinophil-associated mRNA or protein should be elevated relative to those found in unwounded tissue derived from the same anatomical location in a comparable control animal. In this instance "comparable" refers to a second animal of the same species, genetic strain, age, gender and approximate weight as the test subject which has been reared under similar conditions in the laboratory and which was not injured at the site being compared prior to tissue harvesting.

Following the establishment of average baseline levels of the eosinophil-associated protein or mRNA marker of interest, derived from a statistically-significant number of such test and control measurements made using a corresponding number of test and control individuals, candidate inhibitors of eosinophilia can be assayed. A significant reduction in the concentration of the marker below the baseline is indicative of efficacy in inhibiting eosinophil infiltration into wound tissue, the production by such eosinophils as are present in a wound of the given marker protein or mRNA and/or the elimination of that protein or mRNA from the wound.

Administration, Dosage and Pharmacological Formulation of an Inhibitor a. Administration As discussed above, candidate inhibitors should be directed either at the eosinophils themselves or at eosinophil-specific products. Depending upon the intended target of the inhibitor, different routes of administration may be used. In the first case, one must attempt to inhibition at one of two critical steps: (a) the development and/or release of mature eosinophils, which requires that the inhibitor be directed at hematopoietic stem cells via systemic administration of the drug, or (b) recruitment of eosinophils to the wound site. While the latter process is not yet understood, it is anticipated that when the underlying mechanism is elucidated, inhibitory compounds should be directed to the wound site itself, which can be accomplished by systemic or topical administration of the candidate compound. In the second instance, since it is assumed that the products of infiltrating eosinophils are locally present in the wound site, either systemic or topical administration is, again, appropriate.

1. Systemic Administration of an Inhibitor Compound.

In cases in which activity of the inhibitor is required at a site that is remote relative to the that of the wound, systemic administration of a drug is generally appropriate. Methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced inhibitor or may, instead, comprise cells that produce and secrete the inhibitory substance.

Alternatively, systemic administration is advantageous when inhibitor must be delivered to a wound that is accessible to topical application, but in which environment (such as the digestive tract) the native activity of the inhibitor might be compromised, e.g. by digestive enzymes or extremes of pH.

2. Topical Application of Inhibitor

It is contemplated that global administration of the inhibitor to an animal is not needed in order to achieve a highly localized effect. Given that an epithelial wound is, by definition, on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Topical compositions comprising an inhibitor can take any of several physical forms, as summarized below:

(i) A liquid, such as a tincture or lotion, which may be applied by pouring, dropping or "painting" (i.e. spreading manually or with a brush or other applicator such as a spatula).

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the wound or, alternatively, applied as a nebulized spray.

(iv) An liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of an inhibitor.

In a specialized instance, the internal surface is that of the lung. Epithelial injuries to the lung often result from smoke inhalation or other forms of thermal or chemical burning. In such a case the most expedient route of administration for inhibitor is via inhalation, either of a liquid aerosol of (d) or of a nebulized powder of (c). Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin. Invest.*, 84: 1349–1354).

Note that in some cases, the surface in question is internal, for example, the gastric lining; in such a case, topical application would comprise taking the drug via an oral route, whether in liquid, gel or solid form.

b. Dosage

Dosage is calculated based upon the systemic dose demonstrated to be effective. For example, the hamsters of Examples 2 and 3, below, received three 5 mg doses over a period of one week; each dose was, therefore, approximately 58.8 mg/kg of total body weight at the time of administration, based upon a body weight of 85 g. Taking into account the half-life of the native activity of a given inhibitor in blood serum, the mean circulating dosage throughout the week is estimated in mg/kg of total body weight. Such a dosage may range from 10 $\mu$g to 100 mg; preferably, it is from 100 $\mu$to 10 mg. The volume of cells to be treated is then calculated. If administration is to be topical, then V=wound surface area×depth of affected cell layers; otherwise, the whole-body volume of the individual to be treated is estimated. This figure is converted to kg, assuming a density of approximately equal to 1, and the whole body dosage is divided by that number. The concentration of inhibitor in the chosen carrier composition is then adjusted such that the required dosage is delivered in a convenient volume.

c. Pharmacological Formulation

In the case of liquids, ointments and liquid-based aerosols, the preferred solvent is an aqueous medium with an ionic balance that mimics physiological salt levels in order to preserve activity of the inhibitor and to avoid changes in osmotic pressure for the cells to be contacted with the composition. An example of such medium is a low-ionic-strength saline solution.

Lipid-, other hydrocarbon-, fluorocarbon- or halogen-based media also should be formulated such that they maintain a physiological salt balance. While such media may be used according to the methods of the invention, the use on wounds resulting from thermal injury of lipid- and other hydrocarbon-based media is contraindicated. In such cases, fluorocarbon-based media have been shown to be particularly advantageous (see Oxynoid et al., 1994, *Art. Cells, Blood Subs., and Immob. Biotech.,* 22(4): 1331–1336).

Dry powders comprising a protein or carbohydrate may be produced via air-drying of a precipitate or by lyophilization; in some instances, an inhibitor may be an organic or inorganic salt, commercially known and available as a dry powder or as crystals. In either case, it is desirable to compound the inhibitor with a bulking agent, such as are commonly known in the art, for ease of handling.

An inhibitor of eosinophil influx into a wound may comprise a protein, carbohydrate or other bio-degradable substance; therefore, depending upon the route of administration, it may be necessary to encapsulate or buffer it in such a way as to protect it from degradation (for example, by digestive enzymes, acid and base), at least until it reaches its target, by such methods as are well known in the pharmacological art.

The invention is illustrated by the following nonlimiting examples wherein the following materials and methods are employed. The entire disclosure of each of the literature references cited hereinafter are incorporated by reference herein.

Example 1 describes the establishment of a hamster open skin wound model. Example 2 describes the use of an anti-IL-5 monoclonal antibody (TRFK-5) preparation to neutralize IL-5 activities in vivo and its effect on the epithelial wound-healing process in the hamster model. Example 3 presents evidence for the specificity of the effect of antibodies directed at IL-5 on wound infiltration by eosinophils. Example 4 presents additional methods by which the efficacy of candidate inhibitors of eosinophilia can be tested.

While Examples 1 through 4 address the testing of an inhibitor of eosinophilia for its efficacy in enhancing the healing of external cutaneous wounds, epithelial injury occurs internally as well. Such wounds may comprise gastric, intestinal, nasal, oral and tracheobronchial ulcers, vaginal or anal abrasions and thermal or chemical burns to the nasal passages, sinuses, tracheobronchial tubes, lungs, esophagus, stomach or intestinal tract, as well as cutting or piercing wounds, such as from a swallowed sharp object, or a gunshot or knife wound, including a surgical incision. Each of Examples 5 through 8 presents a different animal model in which a candidate inhibitor is administered via any of the several systemic or topical routes detailed above and assessed for efficacy at enhancing internal epithelial wound healing.

EXAMPLE 1

Establishment of a Hamster Open Skin Wound Model

Male Syrian hamsters (LVG strain, 81 to 90 g body weight) were obtained from Charles River Laboratory (Wilmington, Mass.). All hamsters were accompanied by a health report, which certified that they were pathogen-free (viral antigen free/specific pathogen free) and included a listing of the serology, bacteriology, parasitology as well as pathology profiles of the hamsters. No value exceeded the normal range. During the course of the studies there were no indications of helminthic or other parasitic infections, as evidenced by consistent gain in body weight and food/water consumption. All animals were treated according to the *Guide for the Care and Use of Laboratory Animals* (DHHS Publication No. NIH 85–23, revised 1985). Each hamster was kept in a separate cage throughout the experiment.

Fourteen mm full-thickness single circular skin wounds were created on the back of the hamsters between the scapulas. These open wounds healed by re-epithelialization and wound contraction as shown in FIG. 1 (Pincus et al., 1981, *Blood,* 58: 1175–1181), which presents the clinical progression of wound closure in one hamster. These photographs (1:1 magnification) were taken with a Yashica Dental Eye camera oriented perpendicularly above the wound. The periphery of the open wound is marked by black arrows in each frame.

Epithelial closure occurred in ~15 days. Each of the hamster cutaneous wounds was documented daily using photographs, taken as described above. A millimeter ruler was included in each photograph to provide a reference for the measurements. Wound margins were subsequently traced and the surface area of the open wounds was quantified by planimetry using the Metamorph software (version 1.1D18, Universal Imaging Corp., West Chester, Pa.) on an Image-1 computer system. From the 5th day onwards, there was a steady decrease in the wound opening until complete epithelial closure by ~day 15. The wound closure was defined when pressure application of a sterile cotton swab to the wound site did not induce bleeding. The clinical and histological features of hamster cutaneous wound healing are similar to those described in humans and other mammalian models (Ruldolph et al., 1992, *Wound Contraction and Scar Contracture in Wound Healing, Biochemical and Clinical Aspects,* eds. Cohen, I. K., Diegelmann, R. F. and Lindblad, W. J., W.B. Saunders Company, Philadelphia, pp. 96–114). Namely, the continuous and overlapping phases of inflammation, proliferation, and tissue remodeling could be identified.

EXAMPLE 2

The Effect of Inhibitor on Wound-associated Eosinophils and Wound Healing

Following the establishment of the hamster skin wound model, a candidate inhibitor of cutaneous wound healing was tested. In that the biological function of eosinophils that infiltrate a wound was unknown, one could not predict whether a change in their number would help-, hinder- or have no effect upon the healing process. We adopted an experimental approach that employed the anti-IL-5 monoclonal antibody, TRFK-5 (supplied by Dr. Robert Egan, Schering Plough Research Institute). Studies have shown that the administration of TRFK-5 at 1–2 mg per week into mice can ablate the eosinophilia normally seen with helminthic parasite infections (Coffman et al., 1989, *Science*, 245: 308–310; Herndon and Kayes, 1992, *J. Immunol*, 149: 3642–3647; Sher et al., 1990, *Proc. Natl. Acad. Sci. U.S.A.*, 87: 61–65; Sher et al., 1990, *J. Immunol.*, 145: 3911–3916) and to reduce eosinophilia that accompanies allergen-challenged airway hypersensitivity (Mauser et al., 1995, *Am. J. Respir. Crit. Care Med.*, 152: 467–472; Van Oosterhout et al., 1993, *Am. Rev. Respir. Dis.*, 147: 548–552).

A mouse monoclonal antibody (TRFK-5) directed at human IL-5 and control anti-LFA-3 (leukocyte function antigen-3) were kindly provided by Dr. Robert Egan at Schering-Plough Research Institute. Antibodies were prepared from supernatants of serum-free cultures and were more than 95% pure. The purified antibodies were dialyzed into phosphate-buffered saline, concentrated to 10 to 20 mg/ml, and filter sterilized. Thirty two hamsters were randomly divided into two groups of sixteen animals for this study. The protocol of antibody administration for the sixteen hamsters in each group was as follows: Either 1) 5 mg of TRFK-5 or 2) 5mg of control anti-LFA3 was injected intraperitoneally (see Coffman et al., 1989, supra) at three different times, each before wounds were created. In the case of parasitic infection, a period of 7 to 11 days is needed to observe the significant reduction of blood eosinophilia after the administration of TRFK-5 (Coffman et al., 1989, supra); therefore, we administered the antibody 7 and 4 days- and on the same day prior to wounding. The rationale of this schedule was to optimize the effect of anti-IL-5 monoclonal antibody administration in each of the animals undergoing the entire normal cutaneous wound healing process that takes place over a period of approximately 15 days.

Single full-thickness circular cutaneous wounds, 14 mm in diameter, were created to the level of subcutaneous fat in the back between the scapulas in each of the two groups of hamsters after three doses of antibody treatment, respectively. The wounds were left open to air. From each of the two groups of 16 hamsters, 8 animals in each group were sacrificed on day 9, when eosinophil infiltration in hamster cutaneous healing wounds peaks (Wong et al., 1993, supra), in order to evaluate the effectiveness of the use of antibodies directed against IL-5 to deplete eosinophils. Each of the eight wounds harvested was immediately fixed in freshly prepared 4% paraformaldehyde at 4° C. for 2 hours, then dehydrated through increasing percentages of ethanol, then xylene, and finally embedded into a sectioning support. A variety of sectioning support media could have been used, including paraffin, plastic polymers or a mixed paraffin/polymer medium (e.g. Paraplast®Plus Tissue Embedding Medium, supplied by Oxford Labware). In this case, Paraplast®Plus was employed. Particular care was given to ensure optimal orientation to permit the identification of various wound landmarks such as the wound edges and base, and the exudate for histological analysis. The remaining hamsters in each group were monitored until and/or after complete epithelial closure was observed.

Eosinophils were quantified in hamster skin wounds as previously described (Wong et al., 1993, supra). Briefly, sections of 8 μm thickness were cut and mounted onto glass slides. The first two sections from the center of each of the harvested wounds were used for eosinophil quantification. The absolute number of eosinophils in the wound proper was quantified. Each wound was examined using an optical grid at total magnification of 250×. The border of the granulation layer was defined superficially by the exudate layer, on the sides by the transition between normal oral mucosa and wound-associated regenerative epithelium, and at the base by the muscle layer. One field adjacent to each of the lateral borders of the granulation layer was included in the quantification. In order to determine the density of eosinophils in each wound (eosinophils per $mm^2$), the area of each of the wounds was determined by using an eyepiece at 10×magnification, calibrated against a stage micrometer. Identification of eosinophils, based on their characteristic orange-red fluorescence after Fisher Giemsa staining, was accomplished by the use of rhodamine fluorescence microscopy (Wong et al., 1993, supra).

A comparative quantitation of wound healing between the experimental and control groups was conducted using the following parameters: First, quantitation of eosinophils at the harvesting time point was performed. Only the central wound sections were measured. The mean and standard deviation of eosinophil densities (cell numbers per $mm^2$) in wounds of the 8 hamsters in each group were calculated. As determined by this method, the densities of eosinophils infiltrating into day-9 wounds were significantly ($p<0.01$) lower in the experimental group (0.05±0.03) than in the control group (24±13). This is shown in FIG. 2, in which the average (±SD) of eosinophil density, numbers per $mm^2$, from each of the eight animals were plotted. Wound-associated eosinophils in each of the anti-IL-5 monoclonal antibody treated hamsters were depleted to the level comparable to that seen in normal, unwounded hamster skin.

For the purpose of side-by-side comparison, FIG. 3 shows a mirror-image montage constructed from halves of a day-9 anti-IL-5-treated wound (right side) and a control wound (left side). FIGS. 3A and 3B present two magnifications (40× and 100×, respectively) of this montage, in which the original magnification was 100×. The sections were counterstained by Giemsa staining and visualized by rhodamine fluorescent microscopy to detect tissue eosinophils by their cytoplasmic fluorescence (Wong et al., 1993, supra). The wound centers are marked by the white arrows. FIG. 3A, which provides orientation of the wounds in bright-field, serves to outline the wound architecture. FIG. 3B presents the identical regions of sectioned, stained tissue photographed under rhodamine fluorescence optics to highlight tissue eosinophils. Fluorescent cellular bodies identifiable as eosinophils appear at this magnification. Their identity was confirmed by high power examination (600×) of these fields (FIG. 3C, bracketed region of FIG. 3A; FIG. 3D, bracketed region of FIG. 3B), as performed by Wong et al. (1993, supra). Eosinophils were found to infiltrate prominently around day-9 wounds in the control hamster (left) and were seen in clusters surrounding blood vessels and adipose tissues. Few, if any, eosinophils were found in the clot layer or in the muscle at the wound base. In contrast, the number of wound-associated eosinophils in the anti-IL-5 mAb-treated hamsters were depleted to the level that seen in normal, unwounded hamster skin (right).

Figure 4:
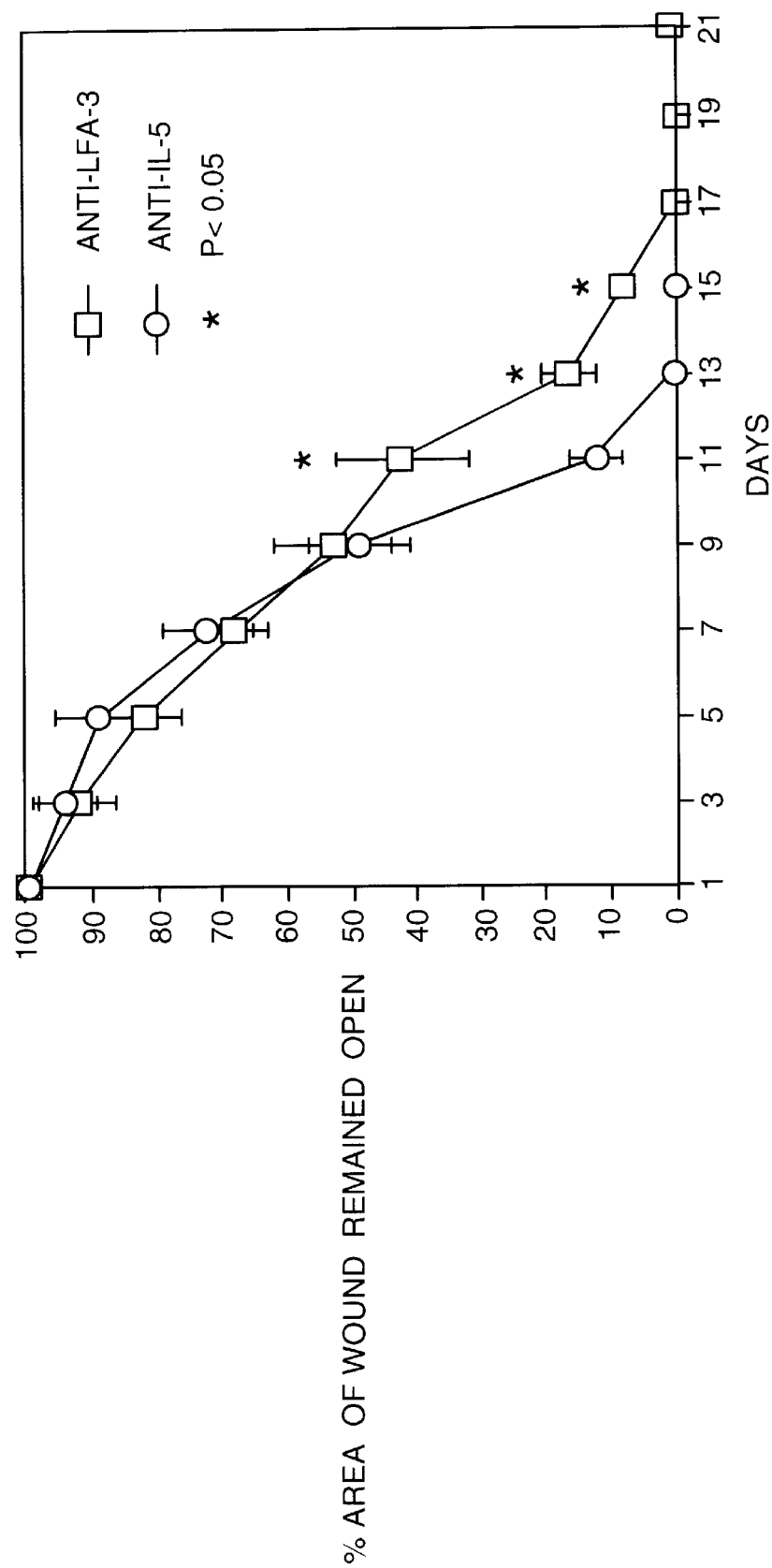
FIG. 4 charts the effect of anti-IL-5 monoclonal antibody treatment on the kinetics of hamster epithelial wound closure.

Planimetry and wound contraction were used throughout the experiment to monitor the re-epithelialization phenotype in both the experimental and control groups. The area of open wounds were monitored and tabulated every other day. This was done by photo-documentation of each wound at the same magnification followed by planimetry. The mean percentage of wounds remained open in each group was calculated, and differences were tested for significance by the Mann-Whitney U test. FIG. 4 presents a graph depicting the re-epithelialization profile of the two groups. Each point represents the average percentage (±SD) of wound size for 8 hamsters of either the treated or control group, which were assessed at each of the indicated time points. The wounds in all the hamsters in the anti-IL-5 mAb experimental group were closed by day 13. In contrast, wounds in the all of the control hamsters required an additional four days to close (day 17). This difference is significant (p<0.05). No significant differences in wound contraction was observed between the two groups (data not shown). In addition, by measuring the area of the granulation tissues between the 2 groups, there is no obvious difference (p<0.05).

The density of the eosinophil infiltrate in the wounds was significantly lower in the experimental group than in the control group (p<0.01). Wound-associated eosinophils in TRFK-5-treated hamsters were abolished to the level of normal, unwounded hamster skin. The progression of wound closure by re-epithelialization in TRFK-5 treated hamsters was 4 days faster than in the control group (p<0.01).

In summary, the data disclosed in this Example represent the first demonstration that the depletion of eosinophil infiltration into skin wounds can be successfully accomplished by the use of the monoclonal anti-IL-5 antibody, TRFK-5, which inhibits IL-5-dependent pathways of eosinophil differentiation and maturation in vivo. The use of a monoclonal antibody directed against IL-5 depleted the number of eosinophils in hamster skin wounds to a level found in unwounded skin. More importantly, this treatment is associated with an accelerated re-epithelialization of cutaneous wounds, with closure occurring four days faster than in untreated control animals (p<0.05). This experiment has been performed twice with the same outcome.

The significant acceleration of re-epithelialization by anti-IL-5 mAb treatment is believed to have clinical implications. Indeed, therapeutic applications of anti-IL-5 mAb is believed to be applicable to facilitating re-epithelialization in humans in selective clinical settings. In a chronic non-healing oral ulcer (traumatic ulcerative granuloma with stroma eosinophilia TUGSE) where there is chronically an abundance of tissue eosinophils, there is always a non-healing, ulcerated mucosa (Elovic et al., 1993, *Oral Surg. Oral Med. Oral Path.*, 81: 672–681). In addition, eosinophils also infiltrate tracheal epithelial wounds (Erjefalt et al., 1996, *Am. J. Respir. Crit. Care Med.*, 153: 1666–74).

EXAMPLE 3
Specificity of the Effect of Inhibitor on Eosinophils

To determine the relative abundance of all infiltrating leukocytes in the wounds, we also quantified other inflammatory cells and mast cells based upon histochemical and morphological criteria after staining of the same tissue sections used for the quantitation of eosinophils, above, with Giemsa stain as per Wong et al. (1993, supra). While eosinophils were identified by their rhodamine fluorescence and nuclear morphology, resident mast cells, as well as inflammatory cells including neutrophils, lymphocytes and pigment-laden macrophages, were identified by their histochemical and morphological characteristics as follows: Neutrophils were identified by their multi-lobed nuclei and lack of rhodamine fluorescence. Cells displaying hyperchromatic nuclei and low cytoplasmic volume were classified as lymphocytes. Mast cells were identified by their metachromatic staining. Monocytes/tissue macrophages are not clearly identifiable by these methods, since morphological features between monocytes/macrophages and fibroblasts and/or endothelial cells in granulation tissue can be difficult to differentiate. Nevertheless, we could readily identify pigment-laden macrophages. Accordingly, we quantified those macrophages which demonstrated phagocytic activity. To determine if the overall inflammatory infiltrate of other inflammatory cells were affected by anti-IL-5 monoclonal antibody treatment, the differences in mean densities of wound-associated inflammatory cells and mast cells between two groups were calculated and tested for significance by the Mann-Whitney U test. The results of this quantitation of inflammatory cells in day-9 hamster skin wounds are shown in Table 1.

TABLE 1

|  | Anti-LFA-3 | Anti-IL-5 | Statistics** |
|---|---|---|---|
| Eosinophils | 24 ± 13†† | 0.05 ± 0.03 | p < 0.01 |
| Lymphocytes | 47 ± 20 | 51 ± 13 | p > 0.05 |
| Macrophages §§ | 116 ± 23 | 108 ± 19 | p > 0.05 |
| Neutrophils | 81 ± 21 | 89 ± 23 | p > 0.05 |
| Mast Cells | 96 ± 26 | 104 ± 27 | 0.03 < p < 0.05 |

**: Mann-Whitney U test
††: Cell Density (Number of Cells per mm$^2$); Mean ± Standard Deviation
§§: Pigment-laden Macrophages The data suggest that eosinophils are specifically depleted in TRFK-5-treated hamster day-9 skin wounds (p<0.01) relative to the other inflammatory cell types (pigment-laden macrophages, lymphocytes and neutrophils), upon whose numbers treatment with TRFK-5 had an insignificant effect. Macrophage densities ranged from 89 to 139 cells/mm$^2$, while those of infiltrating lymphocytes and neutrophils were observed to vary from 27 to 67 and 60 to 112 cells/mm$^2$, respectively. It is also of interest to note that mast cells were found to be more abundant (p<0.05) in 9-day skin wounds of TRFK-5-treated hamsters (104±27) than in those of control animals (96±26). While the importance of this finding remains uncertain, the data do not exclude a compensatory role for epithelial wound closure between the resident mast cells and wound-associated eosinophils in cutaneous wound healing. The use of a mast-cell-deficient model for wound healing studies might address this question.

EXAMPLE 4

In Example 2, the efficacy of one inhibitor of eosinophil infiltration into cutaneous wounds was demonstrated; however, it is necessary to be able to test other compositions which may be of use according to the methods of the invention. While the method presented above will serve for any inhibitor designed specifically to block eosinophilia itself, it is less than adequate for assaying compositions aimed not at blocking eosinophil influx into the wound site or at the elimination of such cells which have already appeared in wound tissue, but instead at blocking an effect of such cells, should they be present in a wound. In order to do this, an animal model system, such as any of those discussed above, is selected, test and control animals are wounded, the candidate inhibitor is administered by any suitable route (see above) and a detection procedure designed to reveal the presence and/or concentration in wound tissue of the target against which the inhibitor is directed (e.g. a cellular product of eosinophils, such as a cell-type-specific mRNA or protein) in both treated and untreated animal subjects at various intervals throughout timecourse of the normal healing process is performed. Detection of a reduction in the target molecule in wound tissue of treated animals relative to that of untreated control subjects is indicative of efficacy of the candidate inhibitor. Examples of several methods, which are applicable in the present invention to detect mRNA or protein in cutaneous wound tissue, are provided herein below. The methods, which have been used previously to detect two cytokine products of eosinophils, TGF-α and TGF-β1 (Wong et al., 1993, supra), may be applied to any desired protein or message.

a. mRNA Analysis of TGF-α and TGF-β1 in Wound Tissue of an Animal Model

Preparation of Nucleic Acid Probes.

In order to monitor the production of an mRNA by eosinophils, oligonucleotides complementary to its sequence for use either to prime nucleic acid synthesis in reverse transcription and PCR or to use as probes in either Northern analysis or in situ hybridization experiments are generated.

PCR Analysis of an Eosinophil-associated Message from Wound Tissue of an Animal Model.

Total RNA is isolated from wound tissue by standard methods. Appropriate primers are designed based upon complementarity to the target mRNA sequence. Any common RT-PCR protocol may be used, such as RNA-PCR (kit no. N808–0017; Perkin-Elmer Cetus, Norwalk, Conn.). Primers may be optimized for annealing efficiency, and selected such that secondary structure and the risk of promiscuous priming are minimized by the investigator, based upon the nature of the target sequence; this complex process may be computer-assisted, using oligonucleotide design programs, e.g. OLIGO™ 4.0 (National Biosciences, Inc.). Following primer synthesis, thirty cycles of PCR are performed using a thermal cycling unit, such as a Perkin-Elmer Cetus DNA thermal cycler, with annealing temperatures optimized for the oligonucleotides being used.

By this method, hamster skin wounds from days 0, 5, 7, and 24 are assayed for mRNA composition. Following isolation of total RNA from wound tissue wounds and the subsequent RNA-PCR reaction for the amplification of the target mRNA, PCR samples are electrophoresed on 2% agarose gels followed by Southern blot analyses using labeled nucleic acid probes complementary to the sequence of that message. 5 μg of total RNA from each of the wound samples is hybridized on a Northern blot to a labeled nucleic acid probe complementary to a housekeeping gene, such as glyceraldehyde-3-phosphate dehydrogenase, as a control to demonstrate the quality and relative quantity of the RNA used. Note that this assay is of sufficient sensitivity not only to detect the presence or absence of these eosinophil-associated messages in wound tissue, but to indicate changes in their levels throughout the timecourse of the experiment. That such modulation is observable is important in assessing the efficacy of inhibitor molecules being tested for use according to the invention, since a candidate inhibitor might be expected to mediate changes in the level of an eosinophil product or in the timing of its expression.

In Situ Hybridization

In situ hybridization, which may also be used to monitor messages produced by eosinophils may also be performed on harvested wound tissue (as described in Example 1) using $^{35}$S-labeled sense and antisense riboprobes under conditions that previously have been determined to permit specific detection of mRNAs in eosinophils (Elovic et al., 1990, supra; Wong et al., 1990, supra; Wong et al., 1991, supra). Examination of the wound sections obtained at the various time points in the healing process reveals the presence and/or concentration of messages expressed by the infiltrating eosinophils, if any, and provides a means by which to assay a candidate inhibitor of eosinophilia.

By this method, wound tissue obtained from test animals to whom a candidate inhibitor of eosinophilia in general, or of a product of eosinophils in particular, has been administered can be compared to that harvested from untreated control animals at intervals over the course of the healing process and compared both for the intensity of labeling of the target message. A significant reduction in message signal level or in the duration of an observable signal is indicative of efficacy of the inhibitor against the target molecule.

b. Analysis of Proteins in Wound Tissue of an Animal Model

Immunological detection of molecules targeted by candidate inhibtors.

Rather than employing methods that are designed to detect mRNAs produced by eosinophils, it is possible to assay eosinophil-associated proteins present in the wound tissues of animals treated with an candidate inhibitor by the methods described above for comparison to those present in the wounds of untreated control animals. A reduction in the amount of target protein is indicative of efficacy of the candidate inhibitor being tested. Immunological detection of a target protein in a protein sample prepared from wound tissue is performed on a Western blot by methods well known in the art; this procedure would employ antibodies specific for the molecule of interest. Examples of such antibodies, which can be directed products of eosinophils, such as the cytokines TGF-α and TGF-β1, are described above, as are general methods of antibody preparation. Alternatively, the detection procedure may be performed immunohistochemically by the direct application to a wound tissue section of antibodies specific for an eosinophil-associated protein. An example of such an immunohistochemical technique, in this case performed on wounded and non-wounded tissue of untreated animals, is provided herein for the purpose of illustration.

Immunohistochemical Detection of TGF-α and TGF-β1 in an animal model.

Immunohistochemistry is used to detect an eosinophil-associated protein in the hamster cutaneous wound-healing model. Primary antibodies directed against the protein of interest (such as TGF-α or TGF-β1) either may be obtained commercially or may be made by the methods described above. A control antibody derived from the same animal species as that in which the primary antibody was raised, such as anti-bacterial protein β-galactosidase (Ab-1; OBO2; Oncogene Science, Uniondale, N.Y.) or the IgGfraction from a nonimmune normal rabbit (I-5006; Sigma Chemical Co., St. Louis, Mo.) is applied at the same concentration as the primary antibody to serve as a negative control. Immunohistochemistry is performed as previously described (Elovic et al., 1990, supra; Wong et al., 1990, supra; Wong et al., 1991, supra). In brief, paraffin-embedded sections of 6 μm thickness are prepared from fixed wound-tissue as in the above Examples, and incubated with an appropriate primary antibody; frozen- or plastic-embedded sections may also be advantageously used. Following incubation and washing, bound antibody/antigen complexes are detected using a secondary antibody directed against the IgG of the host species in which the primary antibody was raised, conjugated to alkaline phosphatase (e.g. that found in the VECTASTAIN® ABC. kit; Vector Laboratories, Burlingame, Calif.) and an alkaline phophatase substrate, such as alkaline phosphatase substrate I (Catalog No. SK-5100, Vector Laboratories, Burlingame, Calif.), after which color development is monitored. A reduction in the amount of the eosinophil-associated protein of interest in test samples derived from animals treated with the candidate inhibitor relative to untreated controls is indicative of efficacy of the drug in inhibiting eosinophilia or an effect thereof.

Sections may be counterstained with 0.2% aniline blue (Sigma, CI 42755), which dye is known to visualize eosinophils by ultraviolet fluorescence microscopy (McCrone et al., 1988, *J. Immunol. Methods,* 114: 79–88), for 10 minutes to permit identification of eosinophils.

EXAMPLE 5

In humans, the efficacy of drugs aimed at healing internal surface wounds is measured by either direct visual examination (for example, in the case of oral wounds; see Khandwala et al., 1997, *Oral Surg. Oral Med. Oral Pathol. Oral Radiol. Endo.,* 83: 222–230) or by any of several indirect visual means. One such indirect method is fiber-optic endoscopy, which has been used successfully to assess the healing of tracheobronchial ulcers resulting from tuberculosis (Rikimaru et al., 1993, *Nippon Kyobu Shikkan Gakkai Zasshi,* 31: 426–430). Endoscopic ultrasonography, also known as dye-contrast endoscopy, has been used to advantage, relative to traditional endoscopic procedures, to assess the effect of drugs aimed at healing- and the prevention of relapse of peptic ulcers in humans (Nebiki et al., *J. Gastroenterology and Hepatology,* 12: 109–114). Other techniques include heavy-metal radiography (such as barium scanning) and magnetic resonanace imaging, among others.

While it is possible to administer a drug to test subjects, e.g. a cohort of ulcer patients, and to measure their rates of wound closure for comparison with untreated control subjects, an animal model for wound healing is useful for preliminary testing.

Any of the several mammals already known to exhibit eosinophil infiltration of surface wounds (rats, rabbits, hamsters and pigs, see above) may serve as the experimental model. Several such systems aimed at the production of internal wounds and the assessment of healing are presented here and below, in Examples 6 through 8. In each case, candidate inhibitors of eosinophilia or its effects can be administered by any of the routes described above. Baseline values for the various parameters by which the rate of healing is judged are established in each model. Test and control animals are then wounded by these methods. A statistically-significant improvement in an index by which the rate of healing is assessed according to a given model is indicative of efficacy of the inhibitor in enhancing internal wound healing.

Chemically-induced Gastric Lesions

Gastric lesions are produced in a controlled manner in rats according Okabe et al. (1971, *Am. J. Dig. Dis.,* 16: 277–284) as presented by Tominaga et al., 1997, *Digestive Diseases and Sciences,* 42: 616–625. In brief, eight-week old male Wistar rats reared under standard conditions are fasted for 12 hours, after which they are anaesthetized and subjected to laparotomy. A round plastic mold (6 mm diameter) is placed tightly on the anterior serosal surface of the antral-oxyntic border. Glacial acetic acid (0.06 ml) is poured into the mold and allowed to remain against the gastric wall for 60 seconds. The solution is then removed, the surface of the treated area is wiped with absorbent paper and the abdomen is closed. Control rats undergo sham surgery (laparotomy under ether anaesthesia followed by closure of the incision without acid treatment). Similar lesions may be produced by the application of a topical irritant, such as 100% ethanol (Konturek et al., 1991, *Eur. J. Pharmacol.,* 195: 347); 1.5 ml of ethanol is administered intragastrically through the orogastric tube, and the rats are anaesthetized 1 hour later to measures the area of gastric lesions.

On days 1, 3, 5, 7, 11, 18, 32 and 60 after production of a gastric lesion, rats are sacrificed by cervical dislocation and gastric ulcerated tissues (total gastric walls including ulcerated area, weighing 100–120 mg) are harvested immediately. Intact gastric tissues (from the same region as ulcerated tissues) are harvested from sham-operated rats. Tissues are rinsed in saline solution, frozen in liquid nitrogen and stored at $-80°$ C. These test and control tissues are used for measurement of wound healing, which is gauged by reductions in surface area at various time points and is said to be complete when scarring extends over the entire wound. They are also used as sources of mRNA and as the substrate for immunohistochemical studies, as described below.

Immunological or Molecular Analysis of Inhibitor Action in an Internal Wound-healing Model The success of the inhibitor in reducing a product of eosinophils, such as a cytokine, is measured either by molecular or biochemical techniques which are well known in the art. In situ analysis of harvested internal wound tissue is performed as described above for external tissue. A protocol for Northern analysis of mRNA that has been advantageously applied to RNA derived from gastric wound tissue is described below, as is an immunohistochemical procedure optimized for gastric tissue. Both are as previously described (Tominaga et al., 1997, supra). Western analysis, performed by techniques well known in the art, may also be employed.

a. The Use of Northern Analysis to Gauge the Efficacy of an Inhibitor of Eosinophilia into a Wound Site.

Total RNA is isolated from rat gastric tissue by procedures well known in the art (see Kim et al., 1994, *Kidney Int.,* 46: 1346–1358). Fifteen $\mu$g of total RNA is electrophoresed on a 1% formaldehyde/agarose gel and transferred to a nylon membrane by standard methods (see Sambrook et al., 1989, *Molecular Cloning. A Laboratory Manual.,* 2nd-Edition, Cold Spring Harbor Laboratory Press, Cold Spring Harbor, N.Y.). A labeled cDNA probe complementary to an eosinophil-associated mRNA and a second labeled probe complementary to the mRNA of a housekeeping gene whose expression level is unaffected by the wound-healing process (e.g. glyceraldehyde-3-phosphate dehydrogenase, or GAPDH), which serves as a control for even loading across lanes of the gel, are incubated with the filter under conditions that will permit specific hybridization of the probe to the target sequence, for example, 50% formamide, 5× Denhardt's solution, 5×SSPE, 1% SDS and $1-2\times10^6$ dpm/ml $^{32}$P-labeled probe. Following hybridization, washes are performed in 2×SSPE at room temperature for 30 minutes, twice in 2×SSPE/2% SDS at 65° for 45 minutes and 0.1 ×SSPE at room temperature for 30 minutes. Other nucleic acid hybridization protocols (e.g. that of Church and Gilbert, 1984, *Proc. Natl. Acad. Sci. USA,* 81: 1991–1995) also may be advantageously employed.

Following hybridization and washes, the bound probe is detected by standard methods, including autoradiography or phosphorimaging. Autoradiography is performed using Kodak XAR-5 film or another standard x-ray film. Signal quantitation may be visual; alternatively, densitometry may be performed using either a densitometer or any of a number of widely-available desktop optical scanners, e.g. a GT-8000 (Epson Corporation; Seoko, Tokyo, Japan) or an Argus II flatbed scanner (AGFA), in conjuction with image-processing programs such as the public-domain NIH Image software (version 1.5, Wayne Rosband, National Institutes of Health, Bethesda, Md.) and a personal computer. The level of expression of the eosinophil-associated message is compared to that of the control message in each lane, and the numerical results are normalized so that a direct comparison of the test message levels in the wounds of treated and untreated animals can be made. A statistically-significant difference in expression levels of the message of interest in treated and untreated subjects is indicative of efficacy of the inhibitor against eosinophil infiltration into the wound site or an effect thereof.

b. Immunohistochemical Detection in Internal Epithelial Tissue of Target Proteins of a Candidate Inhibitor.

Antibodies against inhibitor targets, such as Colony Stimulating Factors or the products of eosinophils, such as cytokines or other molecules, are obtained or prepared as described above for use according to the following protocol.

Intact rat gastric tissue, dissected, rinsed and frozen as described above, is fixed in methyl Carnoy solution or periodate-lysine-formaldehyde for 4–6 hours and embedded in a paraffin or paraffin/polymer sectioning support medium, as described in Example 2, above. Sections of 6 μm thickness are taken, affixed to ovalbumin-coated ("subbed") glass slides, de-paraffinized in xylene and rehydrated through a series of decreasing concentrations of ethanol. After immersion for 30 minutes at room temperature with a pre-immune serum derived from an animal of the same species as that in which the antibody to be used to detect the target protein was raised, sections are incubated for 24 hours at 4° C. with the specific antibody at an appropriate dilution, either that recommended by the supplier or one which is empirically determined via serial dilution of the antibody. Endogenous peroxidase is inactivated by immersing sections in 0.3% $H_2O_2$-methanol for 15 minutes after the incubation with the primary antibody. After washing in phosphate-buffered saline (PBS), sections are incubated with a biotinylated antibody directed against the IgG of the species in which the primary antibody was raised (for example, with a primary antibody raised in rabbits, one may use a goat-anti-rabbit-IgG as a secondary antibody) for 45 minutes at room temperature. Sections are then washed in PBS, incubated with peroxidase-labeled streptavidin for 30 minutes at room temperature and developed in 0.03% 3,3'-diaminobenzidine (DAB) soution with 0.005% $H_2O_2$ and with sodium azide (65 mg/100 ml) to inactivate endogenous peroxidase. Color development is visually monitored and is documented photographically or xerographically. A significant decrease in color development in samples derived from animals treated with a candidate inhibitor is indicative of its efficacy against a given target molecule.

EXAMPLE 6
Ischemia-induced Gastric Lesions

Gastric lesions are produced in rats as previously described (Konturek et al., 1997, *Eur. J. Pharmacol.*, 322: 73–77). Briefly, 180–220 g male Wistar rats are fasted for 18 hours, anaesthetized using an intraperitoneally administered pentobarbital (60 mg/kg), the abdomen is opened by a midline incision and the celiac artery is clamped for 30 minutes, after which time reperfusion is allowed. At 1, 24 and 48 hours following release of the clamp, animals are again anaesthetized and their abdomens opened. The stomach is then removed to measure the area of gastric lesions using computerized planimetry (see Konturek et al., 1991, supra).

A hastening of gastric lesion closure in animals treated with a candidate inhibitor drug relative to control animals given only carrier is indicative of efficacy of that inhibitor in enhancing wound healing. Nucleic acid or protein analyses to detect eosinophil influx or products of eosinophils in a wound site, if desired, are performed as described above.

EXAMPLE 7
Esophageal Corrosive Burns

Corrosive burns were induced and the effects measured in rats by the method of Berthet et al. (1994, *Brit. J. Surgery*, 81: 395–398). 320–380 g male Wistar rats were anaesthetized with 2% xylazine (15 mg/kg) and ketamine (100 mg/kg), administered subcutaneously. After laparotomy, the abdominal esophagus is exposed via dissection for a 1 cm length and isolated between two clamps. A Silastic catheter of internal diameter 1.0 mm and external diameter 2.2 mm (Dow Corning; Midland, Mich.) is then advanced to the upper part of the abdominal esophagus via the mouth and a second Silastic catheter of inner diameter 1.6 mm and outer diameter 3.2 mm is introduced up to the lower part via a gastrotomy. A 2.5 M NaOH solution is infused through the upper catheter for 90 seconds. During the next 15 seconds, the site of the burn is irrigated with 2 ml 0.9 M saline. The catheters are then withdrawn and the gastrotomy and laparotomy sites closed. Post-operatively, the rats are fed ad libitum with a standard oral liquid diet.

During the observation period, each animal is weighed daily; loss of weight correlates with the severity of injury and/or the length of time required for healing. Similarly, as injury produces swelling (stenosis) in the esophagus, the severity of injury correlates with shrinkage in the esophageal bore size, as measured using a Silastic catheter inserted via the mouth. Lastly, microscopic examination of the esophageal tissue at the wound site is performed. Animals are sacrificed by approved means on days 2, 5 and 20 after wounding, and the esophagus and stomach are removed en bloc. The burned area of the esophagus is divided into two parts, one to be used in histological analysis, the other for biochemical analysis (such as protein and nucleic acid studies; see below). Tissue fragments are fixed in formalin solution and embedded in paraffin wax. Three transverse sections of the burned area (upper, medium and lower parts) are taken and then hematoxylin-phloxine-saffron staining is carried out. Edema, inflammation, necrosis and fibrosis in the esophageal wall are graded from mild to severe. Esophageal wall thickness and internal diameter are assessed by examination with a millimetric ocular microscope. A stenosis index (wall thickness: lumen diameter) is calculated. A decrease in edema, inflammation, necrosis, fibrosis or stenosis is indicative of healing; a significant reduction in any of these values in treated animals relative to untreated animals is indicative of the efficacy of the candidate inhibitor at enhancing wound healing.

If a correlation is sought between the rate of healing and the level of the target of the inhibitor being tested, the second half of the wound tissue sample can serve as the source for RNA or proteins, which can be examined either by Northern analysis or in situ hybridization, or by Western blotting or immunohistochemistry using antibodies directed against the target protein, as described above.

EXAMPLE 8
Chemically-induced-colitis

Dextran sulfate (DSS) has been used recently to induce colitis in experimental rodents (Okayasu et al., 1990, *Gastroenterology*, 66: 753–755). DSS is a large molecule which is not easily absorbed by the body; therefore, it is presumed to act topically on the luminal surface of the colonic mucosa after oral administration. To create an animal model of colonic ulcer healing and, consequently, a means for testing candidate inhibitor substances for enhancement of that process, the procedure of Bjorck et al. (1997, *Digestive Diseases and Sciences*, 42: 824–832) is followed; these authors have demonstrated that colonic ulcers induced by DDS mimic those found in humans, in which the mucosal membrane in the colonic lumen is susceptible to permeation by bacterial antigens and other non-cellular toxins, which is illustrated by the uptake of Evans blue (EB) by tissue at the wound site. According to the methods of the present invention, DSS-induced ulcers are created and the candidate inhibitor is administered, either prior to- or after wounding. Decreases in the absolute amount of EB taken up at the wound site or in the number of days over which it is taken up in animals treated with the drug relative to those who receive only carrier is indicative of enhanced wound healing. The protocol can be summarized briefly as follows:

Male Sprague-Dawley rats weighing 235–265 g are fed 5% DSS in their drinking water for seven days under otherwise normal conditions (22° C., a controlled 12-hour light/dark cycle and free access to a standard pellet diet and water). The animals are studied on the eighth day in acute experiments using intraluminal instillation of Evans blue (EB; Sigma Chemical Co., St. Louis, Mo.) and subsequent surgical biopsies of colon. The surgical procedures are performed during a period of 5–10 minutes of ether anesthesia.

In these procedures, the distal ileum is ligated at the junction with the cecum. The proximal cecum is punctured with a needle connected to a 50-ml syringe filled with phosphate-buffered saline (PBS; 145 mM NaCl buffered to pH 7.2 with 70 mM $Na_2PO_4$) at room temperature. Gentle rinsing of the colon is performed to evacuate the fecal contents. A proximal loop (length 4 cm), including the ascending and transverse colon, and a distal loop (length 5 cm), including the descending colon and rectum to a level 4 cm proximal to the anal orifice, are tied off with silk ligatures. A solution of EB (3%) in PBS (total volume 1 ml) is injected into each loop through a fine-needle syringe (0.4 mm outer diameter). The abdomen is then closed with sutures and the colonic loops are exposed to EB for 120 min. The animals are killed by approved methods under ether anesthesia, the colon is dissected out rapidly and the amount of EB that has permeated into the gut wall is assayed as follows:

The colonic loops are opened and three one-minute rinses of the tissue in 6 mM acetylcysteine (KabiVitrum AB; Stockholm, Sweden) in PBS are performed. The midportions of each loop (length 15–25 mm) are then removed, dried on filter paper to remove excess fluid, weighed and incubated with 4 ml formamide ($NHO_3$) at 50° C. for 24 hours in a shaking waterbath. Colorimetric measurements are performed in a spectrophotometer at the peak absorption of 612 nm. Three measurements are performed on each sample, and the mean value is used for calculations, based on extermal standards in formamide. All analyses are performed in a blinded protocol.

Specimens are prepared from unwounded controls and from DSS-exposed animals. When a candidate inhibitor is to be assayed, DSS-exposed animals that have received either the candidate drug or a drug-free carrier will be included in the analysis for comparison. After perfusion with EB and subsequent washing with acetylcysteine, small biopsies of each colonic loop are frozen in liquid nitrogen. Cryostat sections of 5 μm thickness are cut and mounted in DPX mounting medium after drying. The sections are then viewed in an epifluorescence microscope, using a filter combination optimal for the red EB fluorescence (100 W halogen illuminator, 580 nm dichroic mirror, 510- to 560 nm excitation filter and 590 nm barrier filter) to analyze the permeation into control and experimental tissues. Decreased absorption of EB in test animals is indicative of enhanced healing ascribable to the action of the candidate inhibitor.

Immunohistochemical Detection in Colonic Tissue of Target Proteins of a Candidate Inhibitor As used to detect the target protein against which a candidate inhibitor of eosinophil influx into a wound site, or the effects thereof, is directed, the protocol of Bjorck et al. (1997, supra) may advantageously be applied. In short, three specimens from each colonic loop (as defined above) of rats that have undergone induction of colonic ulcers through the application of DSS to the gastrointestinal tract are taken and immediately immersed in cold 4% paraformaldehyde in PBS at pH 7.4. After 4 hours of fixation in this buffer, the specimens are rinsed several times in PBS and in PBS with 10% sucrose, the latter to provide cryoprotection to fine structures during sectioning. The specimens are then frozen, cryostat-sectioned at a thickness of 10 μm and thawed onto gelatin-coated microscope slides. After incubation with an appropriate primary antibody directed against the target of the inhibitor, as defined, obtained and/or prepared as described above, binding is assayed via the indirect method of Coons ("Fluorescent antibody methods", in *General Cytochemical Methods,* ed. J. F. Danielli, 1958, Academic Press, N.Y., pp. 399–422), in which the secondary antibody is coupled to fluorescein isothiocyanate (FITC). The signal intensity, which is directly proportional to the amount of primary antibody bound to the target molecule, can be observed and photographed under a fluorescence microscope; alternatively, the image both can be observed and digitally quantified using a computer-aided confocal microscope. Note that a streptavidin/alkaline phosphatase or a horseradish perosidase labeling system may also be employed. A reduction in the intensity of fluorescence or color development between DSS-exposed animals that have received the candidate inhibitor drug relative to those who have received only carrier is indicative of the efficacy of the inhibitor against the target molecule.

Use

The invention is useful to facilitate the healing of surface wounds by administering an inhibitor of wound infiltration by eosinophils by any of a number of routes after wounding. Alternatively, such an inhibitor can be administered as a pre-emptive measure prior to wounding in such cases, e.g. planned surgical procedures, where wounding is anticipated. In addition, administration of an inhibitor of eosinophil wound infiltration may be useful to prevent or reduce the severity of recurrence of spontaneously-occurring wounds such as ulcers. In view of the lack of eosinophil-deficient animals, the success of a mouse anti-human IL-5 monoclonal antibody in blocking hamster eosinophils into skin wounds provides an animal model that is particularly useful to evaluate the role of the eosinophil in normal and pathological processes.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of enhancing healing of a wound wherein said wound is caused by cutting piercing, abrasion, surgical incision, ulceration, thermal burn, chemical burn, radiation burn or friction burn, comprising administering to a mammal in need thereof an amount of anti-IL-5 antibody into a wound site sufficient to result in healing of said wound.

* * * * *

UNITED STATES PATENT AND TRADEMARK OFFICE
CERTIFICATE OF CORRECTION

PATENT : 6,001,357
DATED : December 14, 1999
INVENTOR(S) : David T. W. Wong, et al It is certified that error appears in the above-identified patent and that said Letters Patent is hereby corrected as shown below:

On the title page, item [73] Assignee, should read as follows:

Assignee: Beth Israel Deaconess Hospital, Inc., Boston;
President & Fellows of Harvard College, Cambridge,
both of Mass.--.

Signed and Sealed this

Thirtieth Day of May, 2000

*Attest:*

Q. TODD DICKINSON

*Attesting Officer*     *Director of Patents and Trademarks*